United States Patent
Lin et al.

(10) Patent No.: US 10,639,466 B2
(45) Date of Patent: May 5, 2020

(54) CONNECTION-FREE FILTER CAPSULE APPARATUS

(71) Applicant: Saint-Gobain Performance Plastics Corporation, Solon, OH (US)

(72) Inventors: ZhenWu Lin, Pasadena, CA (US); Jacob Andrews, Washington, DC (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 648 days.

(21) Appl. No.: 15/075,748

(22) Filed: Mar. 21, 2016

(65) Prior Publication Data

US 2016/0271528 A1 Sep. 22, 2016

Related U.S. Application Data

(60) Provisional application No. 62/136,091, filed on Mar. 20, 2015.

(51) Int. Cl.

| | | |
|---|---|---|
| *B01D 35/30* | (2006.01) | |
| *A61M 39/10* | (2006.01) | |
| *B01D 35/00* | (2006.01) | |
| *B01D 33/327* | (2006.01) | |
| *A61M 16/10* | (2006.01) | |

(52) U.S. Cl.
CPC ........ *A61M 39/1011* (2013.01); *A61M 39/10* (2013.01); *B01D 35/00* (2013.01); *B01D 35/08* (2013.01); *B01D 35/30* (2013.01); *A61M 16/105* (2013.01); *A61M 2205/75* (2013.01); *A61M 2207/00* (2013.01)

(58) Field of Classification Search
CPC .............. A61M 39/1011; A61M 39/10; A61M 16/105; A61M 2205/75; A61M 2207/00
USPC ................................. 210/232, 238, 540, 541
See application file for complete search history.

(56) References Cited

U.S. PATENT DOCUMENTS

| | | |
|---|---|---|
| 5,545,242 A | 8/1996 | Whitlock et al. |
| 5,635,058 A | 6/1997 | Bowman |

(Continued)

FOREIGN PATENT DOCUMENTS

| | | |
|---|---|---|
| EP | 1179154 B1 | 4/2005 |
| EP | 2 422 837 A1 | 2/2012 |

(Continued)

*Primary Examiner* — Thomas M Lithgow
(74) *Attorney, Agent, or Firm* — Lorusso & Associates

(57) ABSTRACT

Disclosed is a tube/tube connector/capsule port assembly that eliminates a connection point in a filter capsule apparatus. A relatively soft tube is thermally or sonically bonded to a relatively hard tube connector that may have a tube receiving bore, frustoconical tube receiving channel or straight tube receiving channel. The tube connector is bonded to a filter capsule port. The manufacturing process can be either a one-step process bonding the tube, tube connector and capsule in one step, or a two-step process that binds the tube to the tube connector in the first step and then binds the tube/tube connector subassembly to a filter capsule housing during the housing's molding procedure. Single and dual-walled tubes may be used as well as single and dual-walled tubes having reinforcing material superposed about or embedded in the tube wall(s). A tube support collar is also disclosed.

20 Claims, 6 Drawing Sheets

(56) References Cited

U.S. PATENT DOCUMENTS

| | | | |
|---|---|---|---|
| 8,858,532 B2* | 10/2014 | Tsunematsu | A61M 39/10 604/535 |
| 2004/0034328 A1 | 2/2004 | Unger et al. | |
| 2005/0072725 A1 | 4/2005 | Swanson | |
| 2005/0082826 A1 | 4/2005 | Werth | |
| 2008/0169646 A1 | 7/2008 | Werth | |
| 2012/0041425 A1* | 2/2012 | Tsunematsu | A61M 39/10 604/535 |
| 2012/0216903 A1 | 8/2012 | Osborne | |
| 2013/0043676 A1 | 2/2013 | Baker | |
| 2013/0264265 A1 | 10/2013 | Lin | |
| 2014/0017372 A1 | 1/2014 | Nabeiro | |
| 2014/0091569 A1 | 4/2014 | Spohn | |
| 2015/0240973 A1* | 8/2015 | Miller | F16L 19/028 285/347 |
| 2016/0271528 A1* | 9/2016 | Lin | B01D 29/114 |

FOREIGN PATENT DOCUMENTS

| | | | |
|---|---|---|---|
| GB | 2 000 685 A | | 1/1979 |
| JP | 2003320037 A | * | 11/2003 |

* cited by examiner

CONNECTION-FREE FILTER CAPSULE APPARATUS

CROSS-REFERENCE TO RELATED APPLICATIONS

A claim of benefit is made to U.S. Provisional Application Ser. No. 62/136,091, filed Mar. 20, 2015, the contents of which are incorporated in their entirety herein by reference.

FIELD OF THE DISCLOSURE

The disclosure relates to filter capsule and tube combinations that eliminate a releasable connection. More particularly, the disclosure concerns combination filter shells, capsules or housings and pliable tubes that eliminate a connection and potential contamination point in a filter assembly.

BACKGROUND OF THE DISCLOSURE

To filter liquids and/or gases of undesired contaminants or impurities, filters and/or purification material, e.g., filter membranes, are used in enclosed filter housings to effectuate contaminant or impurity removal. As used herein, "filter and/or purification material" and/or "filtration material" shall mean any filter membrane, filter media, or any other material or substance used to filter fluids including liquids and gases. To deliver fluids and/or gases to the filter material for filtering, conduits in the form of tubes or pipes are used to deliver the materials to be filtered to a filter capsule containing filter material. As used herein, "filter capsule" shall mean any structure, including, but not limited to, housings, shells, disc filters, filter cages, filter cartridges and the like used to enclose filter material. The conduits can be rigid pipe or pliable tubes made from such materials as thermoplastic elastomers (TPE). For rigid pipe, connectors such as clamps, threaded couplings and the like can be used. For soft pliable tubes, hose bards are the conventional connection choice. Each form of connection includes several drawbacks.

Rigid connectors add considerable cost and spatial inflexibility to the filter assembly, particularly with the use of tri-clamp arrangements that use a clamp to secure flanged ports with flanged tubes. The use of flanged tubes creates at least two potential contamination points. The first is the junction of the flange to the tube. In some available versions, such as those offered by Saint-Gobain, if the seal between the hard plastic or metallic flange and relatively soft tube is in any way compromised, contaminants, such as bacteria, could potentially enter the filter assembly, or, depending upon the application, permit the exit of bacterial contaminants from the filter assembly.

A second point of potential contamination is the clamp/flange juncture. Any damage to the seal between the two adjoining surfaces also could lead to potential contaminant infiltration of the filter assembly. Such events can occur with multiple filter sterilization cycles that may involve high heat or gamma radiation. The use of different materials for the tubes and connectors, each material having different characteristics, e.g., melting points, can have different reactions to sterilization procedures and lead to compromised seals.

Barbs are notoriously prone to connection failure. By design, a barb, over which a tube is secured, exposes an inner wall of a tube to defined annular or segmented acute edges that dig or bite into the tube material. This inevitably weakens the tube at the connection point and can lead to tube failure, particularly if the filter assembly and tube(s) are pressurized. Barb accessory components such as barb lock systems can further add to the mechanical stress placed on the tube at the barb connection. Pressurization of a filter system can add additional stress to the tube/barb connection and can lead to tube deterioration and connection failure. Mechanical stress on the barb connection may also occur with movement of the filter assembly while the tube is connected to the assembly. Any of these potential sources of stress on the tube/barb connection can lead to contaminant infiltration or exit, depending upon the location of the tube and its assigned purpose (inlet, outlet or vent). What is needed is a soft tube filter assembly connection that eliminates the need for any clamping, or barb connection systems so as to eliminate potential contamination points.

What is needed is a tube/tube connector/capsule combination that eliminates a connection point between a relatively soft tube and a relatively rigid port that can withstand manufacturing processes as well as post-use sterilization procedures so as to maintain structural and seal integrity. What is also needed is a tube connector that improves the structural integrity of the tube/capsule connection point so as to rigidity the tube end secured to the capsule. These and other objects of the disclosure will become apparent from a reading of the following summary and detailed description of the disclosure as well as a review of the appended drawings.

SUMMARY OF THE DISCLOSURE

In one aspect of the disclosure, a capsule apparatus for enclosing filters includes a plurality of ports extending from the capsule body to receive liquid and/or gas delivery and exit tubes. The ports are dimensioned to receive the inner and/or outer diameters of the tubes. The dimensions of the port passages are further set to maintain a consistent, continual cross-sectional diameter substantially the same as the cross-sectional diameter of the tube lumen at a relaxed, or unstressed, portion of the tube to be secured to the port.

In another aspect of the disclosure, a tube connector is formed with an annular channel dimensioned to receive an end of a tube. The interior and exterior walls of the channel register against the interior and exterior walls of the tube so as to provide maximal support to the tube end. The tube is bonded to the connector to from a tube/connector subassembly for subsequent bonding to a capsule assembly.

In a further aspect of the disclosure, a tube, tube connector and filter capsule are bonded together in a single step. The connector has portions defining a first bore to receive the outer wall of the tube and a second bore dimensioned to receive a filter capsule port. In an alternative embodiment, the outer wall of the connector is dimensioned to receive the inner wall of a tube as well as an inner wall of the capsule port. In a further alternative embodiment, the connector has a bore to receive a tube end and has an outer diameter dimensioned to receive and register against an inner wall of a port. In a still further alternative embodiment, the connector has an outer diameter dimensioned to receive an inner wall of a tube and a bore to receive an outer wall of the capsule port.

In a still further aspect of the disclosure, a tube connector/barb has portions defining a tube receiving annular channel at a proximal end whereby the inner and outer walls defining the channel are dimensioned to receive the inner and outer walls of a tube. A distal end of the connector is formed in the shape of a barb. In an alternate embodiment, the inner wall defining the annular channel is formed with an increasing diameter at an end distal from the main body of the connector, frustoconical in cross-section, to provide a tube binding surface for a combination mechanical/friction fit to further secure the tube engaged to the connector. In yet another alternate embodiment, a bore is formed in the connector dimensioned to receive and register against an outer wall of the tube.

In yet a further aspect of the disclosure, a tube/connector/capsule port connection is formed in a single step. The connector is formed with an annular channel dimensioned to receive the annular wall of a capsule port. The connector further defines a through bore having a cross-sectional diameter dimensioned to maintain a consistent, continual channel similar in dimension to the cross-sectional diameter of the tube lumen at a portion of the attached tube measured at a relaxed, or unstressed, portion of the tube. In one embodiment, the connector defines a tube bore dimensioned to receive the outer wall of a tube end. In an alternative embodiment, the connector defines a second annular channel, the walls of which are spaced to receive and register against the inner and outer wall of a tube end. In a yet further alternative embodiment, the connector has an outer wall dimensioned to receive the inner wall of a tube end.

In yet another embodiment, a tube/connector/capsule port assembly is bonded in one step. The connector defines an annular channel with an inner wall having a frustoconical shape in cross-section whereby the wider portion of the inner wall extends away from the main body of the connector to provide a mechanical/friction fit to more securely engage the tube. The tube/connector/port assemblies can be dedicated to a particular function, e.g., ingress (inlet), egress (outlet) and exhaust (vent).

In a yet further aspect of the disclosure, a tube/connector/capsule port assembly is bonded in one step. The connector defines a bore with an annular wall dimensioned to receive an outer annular wall of a capsule port. An opposite end of the connector can be formed with an annular channel dimensioned to receive a tube, with an inner wall of the annular channel having a frustoconical cross-sectional shape with the larger diameter end extending toward a tube connecting end of the connector, with a bore dimensioned to receive an outer wall of the tube, or with an outer diameter dimensioned to be inserted into a tube. The connector further defines a channel dimensioned to have substantially the same cross-sectional diameter as the cross-sectional diameter of the tube lumen at a relaxed or unstressed, portion of the attached tube.

In another aspect of the disclosure, a dual-walled, optionally reinforced tube is incorporated into the tube/connector/capsule embodiments disclosed herein. A connection end of the tube is modified to remove an end segment of the outer tube wall to maximize the tube sealing surface area and to minimize a potential contamination point in a dual-walled tube.

In yet another aspect of the disclosure, a tube connection reinforcement or support collar is formed on an end of a tube connector/over-mold to protect the connector/tube junction distal from the capsule. These and other aspects of the disclosure will become apparent from a review of the appended drawings and a reading of the following detailed description of the disclosure.

DETAILED DESCRIPTION OF THE DISCLOSURE

Figure 1:
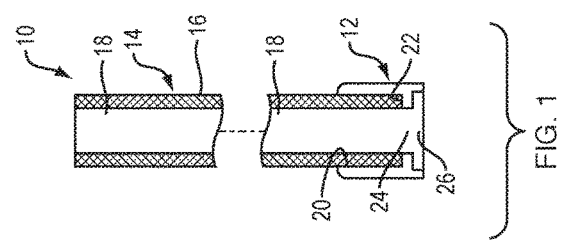
FIG. 1 is a side partial sectional view of a tube/tube connector subassembly according to one embodiment of the disclosure.

Referring to FIG. 1, in one aspect of the disclosure, a tube/connector assembly shown designated generally as 10 includes a tube designated generally as 14 secured to a tube connector designated generally as 12. Tube 14 has an annular wall 16 that defines a lumen 18. The tube is constructed from a thermoplastic elastomer to take advantage of the multiple advantageous characteristics of this material that impart a combination of flexibility and resiliency. An additional advantage is that the material has no reactivity with respect to most liquids and gases that may be passed through the tube. The tube may or may not include reinforcement materials, e.g., fiberglass or metallic braids, on the exterior or embedded in the material to improve resiliency characteristics and to counter any torsional, compression and flexion stresses placed on the tubing.

Connector 12 has an annular wall 20 that defines a smooth tube bore 24 dimensioned to receive and register against an outer wall of tube 14. An annular shoulder 22 is formed at a bottom end of bore 24 and extends radially inwardly from an inner surface of connector wall 20 to form a mechanical stop for the tube when inserted into connector 12. A second capsule bore 26 is formed on a bottom end of connector 12 and dimensioned to receive a capsule port or port stem (disclosed in more detail below. Capsule bore 26 is in fluid communication with tube bore 24 and tube lumen 18 when the tube is secured to the connector.

Tube/tube connector assembly 10 is structured to be bonded directly to a capsule port and may be formed in a two-step process whereby the tube and connector are bonded (thermal, sonic and/or solvent bonding) in a one-process step and the tube/tube connector assembly is bonded to the capsule in a second process step (injection molded, insert molded, and/or any of the thermal, sonic and/or solvent bonding methods used to secure the tube to the tube connector). In an alternative embodiment, the tube, tube connector and capsule port are bonded together in a single processing, step such as injection molding, whereby the material used to form the tube connector is over-molded onto the capsule port and the tube.

It should be understood that any combination of bonding methods and steps can be used to achieve the final connection-free filter apparatus. For example, both thermal and solvent bonding methods may be used together to secure a soft flexible tube to a rigid plastic connector or filter capsule. It may also be advantageous to use a tube material with a lower melting point than that of the material used to make the relatively rigid plastic connector and/or filter capsule so as not to compromise the integrity of the rigid plastic connector with over-heating. It should be further understood that a soft, flexible tube (made from a thermoplastic elastomer or other pliable material) may be secured directly to a filter capsule using any of the molding/bonding methods disclosed herein.

Tube 14 may be constructed from materials including, but not limited to, thermoplastic elastomers (TPE), thermoplastic rubbers (TPR), silicone, PVC, PVS and the like, and any soft and flexible tubing currently used in the pharmaceutical and medical fields. The connector may be constructed from materials including, but not limited to, polyethylene (PE), polypropylene (PP), high density polyethylene (HDPE), nylon, polyvinylchloride (PVC), polyethylene terephthalate (PET), Hytrel type material, and the like. When materials such as TPE are used for the tubing, simple thermal bonding may be used to secure the tube to a tube connector or directly to the filter capsule. For materials such as PVC for the tubing, solvent bonding may be used to secure the tubing directly to the filter capsule.

Figure 14:
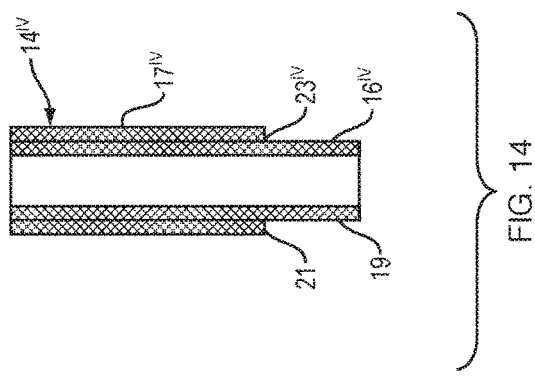
FIG. 14 is a side sectional view of a modified dual-walled reinforced tube according to a further embodiment of the disclosure.
Figure 13:
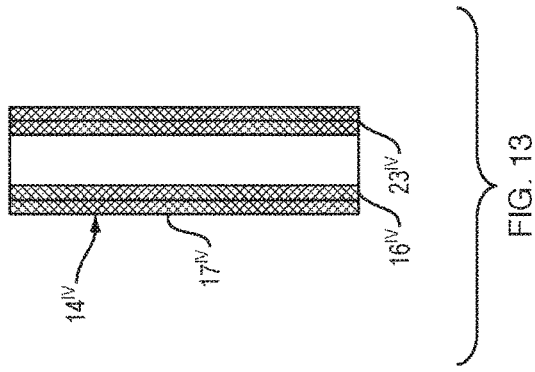
FIG. 13 is a side sectional view of a dual-walled reinforced tube according to another embodiment of the disclosure.

Tube/connector assembly 10 may also be constructed with a dual-walled, reinforced tube such as tube $14^{IV}$ shown in FIGS. 13 and 14, particularly when the tube and larger assembly will be used in a high pressure system in which higher pressure tolerances are needed in the tube component. From a manufacturing perspective, the primary difference between single and, dual-walled tubes is the dimensional considerations of using a tube with a different cross-sectional diameter. Each component is sized to accommodate a different tube diameter including the over-molding material used to form connector 12.

Figure 16:
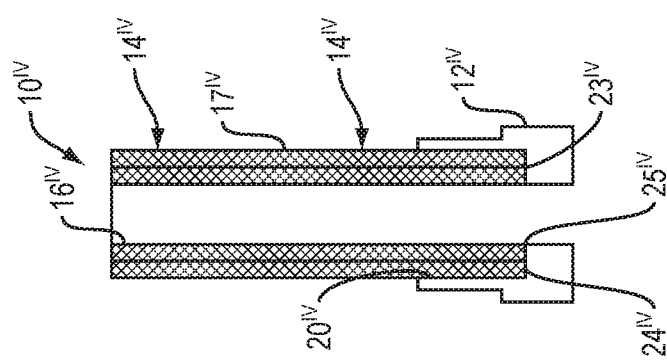
FIG. 16 is a side sectional view of a dual-wailed reinforced tube/tube connector subassembly according to yet another embodiment of the disclosure.

Tube $14^{IV}$ may be formed with any of the materials used to form tube 14 as disclosed herein. The tube reinforcement material may be any commonly used in the art to reinforce tubing material including illustratively, and not exhaustively, braided fiberglass, metallic materials, fibrous material such as cotton, and polymer materials such as polyester, nylon, polyethylene, polypropylene and the like. In one embodiment, tube $14^{IV}$ may be secured to tube connector $12^{IV}$, as shown in FIG. 16, with the same methods described for securing tube 14 to connector 12. If secured in the form shown in FIG. 13, the tube end is inserted into tube bore $24^{IV}$ and registered against connector wall $20^{IV}$. FIG. 16 shows tube $14^{IV}$ secured in connector $12^{IV}$. Connector $12^{IV}$ may be pre-formed and subsequently bonded to tube $14^{IV}$, or may be formed in a mold about tube $14^{IV}$ using illustratively, conventional injection molding processes. It should be understood that the same processing options are available to join the tube and connector to a capsule port/port stem as disclosed herein.

If constructed with the dual-wall extending the entire length of the tube as shown in FIG. 16, although a secure bond between the tube and connector may be formed, there is a potential for contamination between the tubes at the dual-tube end junction with the connector (designated gap $23^{IV}$ in FIG. 16), particularly if the reinforcement material superposed about the tubes contributes to the formation of a gap between the tubes. The connector material should flow into the gap during connector formation and seal it off from any liquids or gases introduced to, and/or exiting from, the capsule through the tube. This requires, however, the bulk material of the braided section to have similar properties as the inner tube material and be thermally bonded by the over-molded connector material. If made of material with dissimilar properties, the reinforcement material should be removed before the over-molding process. This will improve the bond and further help prevent the potential release of undesirable extractables from the reinforcement material.

This problem is potentially exacerbated by the relatively small contact surface area $25^{IV}$ between the inner tube $16^{IV}$ end and an annular shoulder $24^{IV}$ of the connector that leaves little room for error in the molding process and is the only bonded section between the tube lumen and gap $23^{IV}$. If there is any failure of the joint, liquids and/or gases can migrate into gap $23^{IV}$, particularly if the system is pressurized. Fluid migrating into the gap under pressure potentially can create tube failure points (tube burst events) in the tubing. Moreover, exposure of the reinforcement material to the fluid may cause product changes on the wetted surfaces of the material that can affect chemical compatibility among the component materials and may negatively impact regulatory compliance if extractables from the reinforcement material leeches into the fluid and into the tube lumen. A modification of tube $14^{IV}$ significantly improves the contact surface area between inner tube $16^{IV}$ and connector $12^{IV}$ and significantly reduces the possibility of fluid migration into gap $23^{IV}$.

Figure 17:
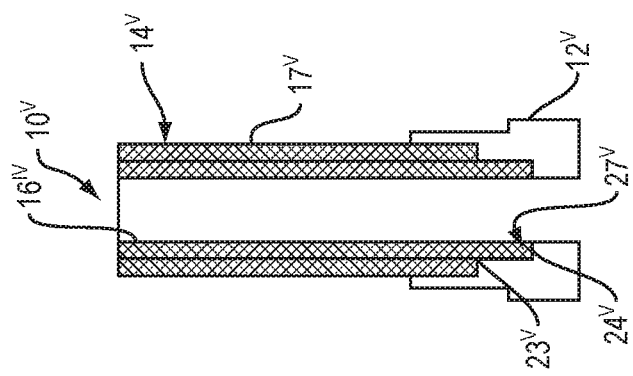
FIG. 17 is a side sectional view of a dual-walled reinforced tube/tube connector subassembly according to still another embodiment of the disclosure.

As shown in FIG. 14, tube $14^{IV}$ may be modified by removing a segment of outer tube $17^{IV}$. This moves gap $23^{IV}$ between the tubes away from the end of inner tube $16^{IV}$ that bonds with an annular shoulder of a connector (shoulder $24^{V}$ shown in FIG. 17). This may or may not include removal of the reinforcement material superposed about inner tube $16^{IV}$ as disclosed above. As shown in FIG. 17, when secured to a connector $12^{V}$, the surface area $27^{V}$ of inner tube $16^{V}$ at contacts connector $12^V$ includes the tube end and the outer wall up to the new end of outer tube $17^V$. This maximizes the surface area of contact and moves the gap $23^V$ between the tubes away from the junction between inner tube $16^V$ and shoulder $24^V$ of connector $12^V$.

To further increase the bond surface area and further eliminate the potential for leakage at the connector/tube junction, any reinforcement material, formed on the exterior of inner tube $16^V$, on the inner tube section exposed by the removal of the outer tube segment, may be removed to present a smooth, maximized contact surface to bond to the connector material. This also is particularly warranted if the reinforcement material has chemical and/or processing properties incompatible with the tube material with respect to bonding to the connector material. It should be understood, however, that removal of the reinforcement material is not a mandatory requirement to form a secure bond between the inner tube and connector material. It is an optional measure that can be taken to reduce the probability of bond imperfections and the release of extractables at the connector/tube junction.

Figure 2:
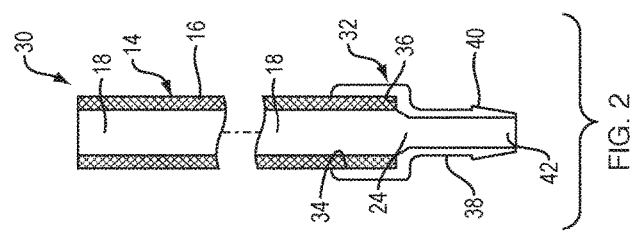
FIG. 2 is a side partial sectional view of a tube/hose barb assembly according to another embodiment of the disclosure.

Referring now to FIG. 2, in another aspect of the disclosure, a tube/barb connector assembly shown designated generally as 30 includes a tube designated generally as 14 secured to a barb connector designated generally as 32. Like connector 12, barb connector 32 has an annular wall 34 that defines a tube bore dimensioned to receive and register against the outer wall of tube 14. A barb connector shoulder 36 extends radially inwardly from wall 34 to form a stop against which an end of tube 14 registers. A distal end of barb connector 32 is formed as a barb connection 38 with at least one radially extending barb 40. Barb connection 38 defines a barb lumen 42 dimensioned to be substantially similar in dimension to lumen 18 of tube 14.

Tube 14 is secured to barb connector 32 in the same manner disclosed for tube/tube connector assembly 10. The materials used to construct barb connector 32 are the same materials disclosed for tube connector 12. The methods used to secure tube 14 to barb connector 32 are the same as those disclosed for tube/tube connector assembly 10. The barb permits connection to other tubes used to deliver or receive liquids and/or gases depending upon the functional assignment given to the tube/barb connector assembly, i.e., inlet, outlet, vent.

Like tube/tube connector assembly 10, barb connector 32 may be secured to a dual-walled, reinforced tube such as dual-walled tube $14^{IV}$ shown in FIGS. 13 and 14. Again, the primary difference is the dimensional modifications needed to receive a tube with a different cross-sectional diameter. The materials and methods used to secure tube $14^{IV}$ to connector 32, and the considerations that impact such a combination, are the same as those disclosed for the combination of tube $14^{IV}$ with connector $12^{IV}$.

Figure 3:
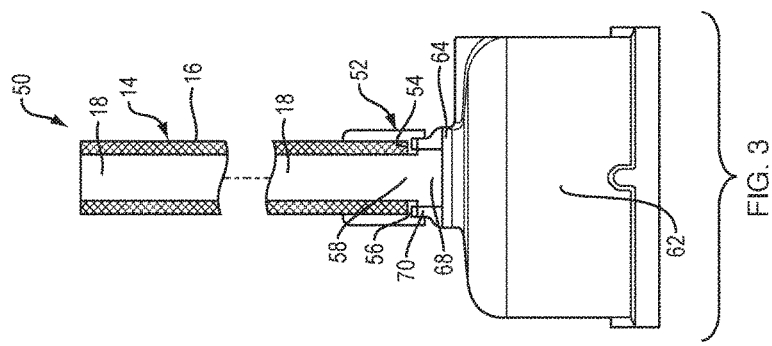
FIG. 3 is a side partial sectional view of a filter capsule/tube/tube connector assembly according to one embodiment of the disclosure.

Referring now to FIG. 3, in a further aspect of the disclosure, a tube/tube connector/capsule assembly shown designated generally as 50 includes a tube 14 secured to a tube connector 52 secured to a capsule port 70. Tube 14 and connector 52 are identical in structure, materials and bonding methods to those disclosed for tube/tube connector assembly 10. Tube connector 62 has a wall 51 that defines a tube bore 58 dimensioned to receive and register against the outer surface of tube wall 16. A shoulder 54 that extends radially inwardly from an inner surface of wall 51 functions as a stop and registration surface for tube 14 when the tube is inserted into and bonded to connector 52.

A port channel 68 defined by port 70 and port base 64 is in fluid communication with tube lumen 18 and with the filter chamber defined by capsule 62. The cross-sectional diameter of channel 68 is dimensioned to be substantially the same as, or not less than the cross-sectional diameter of the tube lumen defined by an unstressed, relaxed segment of tube 14. As shown in FIG. 3, capsule 62 represents one end of a complete capsule, the remainder of which is not shown for purposes of simplicity. It should be understood that the remainder of the capsule housing will include additional ports that may be configured with tube/tube connector assemblies.

An annular port channel 56 is formed on a distal end of connector 52 and is dimensioned to receive the annular wall of port 70 such that the inner and outer surfaces of the wall register against the walls of annular bore 56. A top surface of the port wall is further registered against a bottom surface of bore 56 so as to function as a stop and support surface for the joined components.

The materials used to manufacture the tube, tube connector and capsule are the same as those disclosed for tube 14 and tube connector 12 hereinabove. Tube/tube connector/capsule port assembly 50 may be formed in a one-step or two-step process. In the two-step process, the tube and connector are bonded together using thermal, sonic and/or solvent bonding techniques. The tube/tube connector subassembly is then secured in a mold used to make the capsule and is bonded to the capsule port during the capsule molding process. Alternatively, the tube/tube connector subassembly can be bonded to the pre-formed capsule via thermal, sonic and/or solvent bonding.

In the one-step process, the tube, pre-formed tube connector and capsule are bonded together in a single molding step, e.g. insert molding, wherein the tube and pre-formed tube connector are assembled together and placed in the capsule mold prior to the capsule molding process. Alternatively, the three components can be bonded together in a single thermal, sonic and/or solvent bonding method. Either the one-step or two-step processes produce tube/tube connector/capsule port connections that can withstand pressurized applications as well as post-use sterilization procedures using high heat and/or gamma radiation. The tube connector provides the added benefit of rigidifying and strengthening the end of the tube connected to the connector/port combination. This is in contrast to the weakening effect a barb has on the end of a tube connected to the barb.

Like tube/tube connector assembly 10, barb connector 52 may be secured to a dual-walled, reinforced tube such as dual-walled tube $14^{IV}$ shown in FIGS. 13 and 14. The primary difference continues to be the dimensional modifications needed to receive a tube with a different cross-sectional diameter. The materials and methods used to secure tube $14^{IV}$ to connector 52, and the considerations that impact such a combination, are the same as those disclosed for the combination of tube $14^{IV}$ with connector $12^{IV}$.

Figure 4:
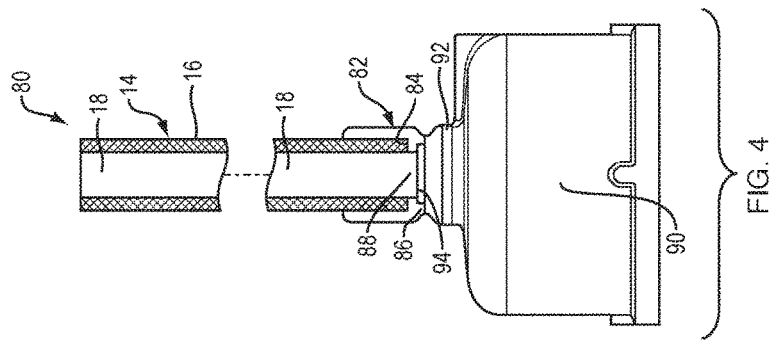
FIG. 4 is a side partial sectional view of a filter capsule/tube/tube connector assembly according to another embodiment of the disclosure.

Referring, now to FIG. 4, in a still further aspect of the disclosure, a tube/tube connector/capsule port assembly is shown designated generally as 80. Assembly 80 includes tube 14, a tube connector designated generally as 82 and a capsule designated generally as 90. Connector 82 has the same features and is structured in the same manner as tube connector 12 shown in FIG. 1. Connector 82 has a connector wall 83 that defines a tube bore 88 dimensioned to receive and register against the outer surface of tube wall 16. A shoulder 84 extends radially inwardly from connector wall 83 and forms a stop/registration surface for the end of tube 14. The cross-sectional diameter of bore 88 substantially maintains the cross-sectional diameter of the lumen of tube 14 taken at a relaxed, unstressed portion of the tube.

A bottom end of connector 82 has an annular wall 86 that defines bore dimensioned to receive the outer wall of capsule port 94. This connector/port connection differs from the connector/port connection shown in FIG. 3 in that connector 82 does not define an annular channel to receive the inner and outer surfaces of the port wall, but just a bore to receive and register against the outer surface of the port wall. This provides a less robust connection, but an adequate one to handle the applications to which the capsule is put to use as well as the post-use sterilization procedures. Like tube/tube connector/capsule port assembly 50, tube/tube connector capsule port assembly 80 can be constructed from the same materials disclosed for the components of assembly 50 in either a one-step or two-step process such as those disclosed for assembly 50. By way of illustration and not limitation, the tube may be injection molded directly onto the filter capsule.

Figure 15:
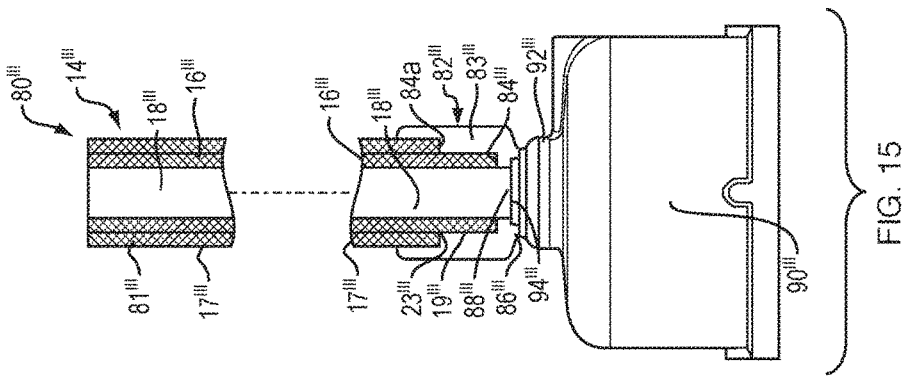
FIG. 15 is a side partial sectional view of a dual-walled reinforced tube/tube connector/filter capsule assembly according to a still further embodiment of the disclosure.

Like tube/tube connector assembly 10, barb connector 82 may be secured to a dual-walled, reinforced tube such as dual-walled tube 14$^{IV}$ shown in FIGS. 13 and 14. The primary difference is the dimensional modifications needed to receive a tube with a different cross-sectional diameter. The materials and methods used to secure tube 14$^{IV}$ to connector 82, and the considerations that impact such a combination, are the same as those disclosed for the combination of tube 14$^{IV}$ with connector 12$^{IV}$. FIG. 15 shows a dual-walled tube secured to the filter capsule configuration shown in FIG. 4.

Referring to FIG. 15, in a yet another aspect of the disclosure, a tube/tube connector/capsule port assembly is shown designated generally as 80'''. Assembly 80''' includes dual-walled tube 14''' (with optional reinforcement material 81'''), a tube connector designated generally as 82''' and a capsule designated generally as 90'''. Tube 14''' comprises an inner tube 16''' and an outer tube 17''' superposed about inner tube 16'''. Reinforcement material 81''' is formed about the tubes and creates a gap 23''' between the tubes where the reinforcement material of the respective tubes register against one another. It should be understood that the optional reinforcement material 81''' may be formed on one or both tubes, or may be imbedded in one or both tubes as well as configured with any combination of surface mounted and imbedded variations. A segment 19''' of inner tube 16''' is not superposed by outer tube 17'''

Connector 82''' has the same features and is structured in the same manner as tube connector 12 shown in FIG. 1 modified, however, to accommodate a stepped, dual-walled tube. Connector 82''' has a connector wall 83''' that defines a tube bore 88''' dimensioned to receive and register against the outer surface segment 19''' of inner tube wall 16'''. An annular shoulder 84''' extends radially inwardly from connector wall 83''' and forms a stop/registration surface for the end of inner tube 16'''. The cross-sectional diameter of bore 88''' substantially maintains the cross-sectional diameter of the lumen of tube 14''' taken at a relaxed, unstressed portion of the tube. A second annular shoulder 84a extends radially inwardly from connector wall 83''' and forms a stop/registration surface for the end of outer tube 17'''. The bonding surfaces between the tubes, the connector shoulders and the exposed segment 19''' of inner tube 16''' create a significant structural separation of tube gap 23''' from the junction of the end of inner tube 16''' with shoulder 84'''. This effectively eliminates the possibility of fluids in the tube lumen entering the inter-tube gap.

A bottom end of connector 82''' has an annular wall 86''' that defines a bore dimensioned to receive the outer wall of capsule port 94''' and register against port base 92'''. This connector/port connection differs from the connector/port connection shown in FIG. 3 in that connector 82''' does not define an annular channel to receive the inner and outer surfaces of the port wall, but just a bore to receive and register against the outer surface wall. This provides a less robust connection, but an adequate one to handle the applications to which the capsule is put to use as well as the post-use sterilization procedures. Like tube/tube connector/capsule port assembly 50, tube/tube connector/capsule port assembly 80''' can be constructed from the same materials disclosed for the components of assembly 50 in either one-step or two-step process such as those disclosed for assembly 50. By way of illustration and not limitation, the tube may be injection molded directly onto the pre-formed filter capsule.

Figure 5:
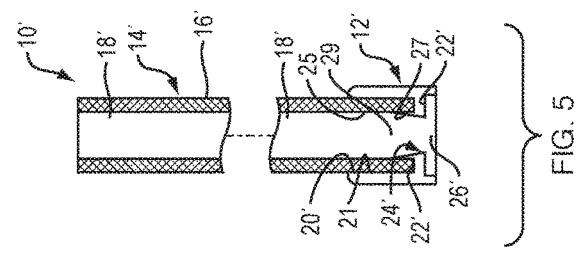
FIG. 5 is a side partial sectional view of a tube/tube connector subassembly according to a further embodiment of the disclosure.

Referring to FIG. 5, in another aspect of the disclosure, a tube/connector assembly shown designated generally as 10' includes a tube designated generally as 14' secured to a tube connector designated generally as 12'. As used herein, elements referenced with primed numbers in one embodiment correspond to elements in other embodiments referenced with the same number either unprinted or primed differently. Tube 14' has an annular wall 16' that defines a lumen 18' like tube 14 disclosed herein.

Connector 12' has an annular wall 20' that defines a tube bore dimensioned to receive and register against an outer wall of tube 14'. A bottom end of the tube bore is formed as an annular tube channel 21 that includes an annular channel bottom 22' that extends radially inwardly from an inner surface of connector wall 20' to form a mechanical stop for the tube when inserted into connector 12'. An inner channel wall designated generally as 24' defines the inner portion of the tube receiving channel and is formed to have a frusto-conical profile in cross-section whereby the larger diameter end of the wall, designated 25, extends upwardly toward the tube bore and the smaller diameter end of the inner wall, designated 27, connects to channel bottom 22'. This configuration creates a mechanical restriction surface that mechanically locks tube 14' into the tube channel and bore. When thermal bonding is applied and the tube material is allowed to flow and expand in the channel, the tube is mechanically locked to connector 12' by virtue of the restricting surface of inner channel wall 24'. The cross-sectional diameter of a tube bore 29 defined by an inner surface of inner wall channel 24' may be dimensioned at its most narrow point to be substantially similar to, or essentially not less than the cross-sectional diameter of the tube lumen at a relaxed or unstressed segment of tube 14'.

A second capsule bore 26' is formed on a bottom end of connector 12' and dimensioned to receive a capsule port (disclosed in more detail below. Capsule bore 26' is in fluid communication with a tube bore 29 (defined by an inner surface of channel inner wall 24') and tube lumen 18' when the tube is secured to the connector. Tube/tube connector assembly 10' is structured to be bonded directly to a capsule port and is formed in a two-step process whereby the tube and connector are bonded in one process step and the tube/tube connector assembly is bonded to the capsule in a second process step. In an alternative embodiment, the tube, tube connector and capsule port are bonded together in a single processing step when the capsule is molded as disclosed more fully herein.

Tube 14' may be constructed from same materials disclosed for tube 14. Tube connector 12' may be constructed from the same materials disclosed for tube connector 12.

Like tube/tube connector assembly 10, barb connector 12' may be secured to a dual-walled, reinforced tube such as dual-walled tube $14^{IV}$ shown in FIGS. 13 and 14. The primary difference is the dimensional modifications needed to receive a tube with a different cross-sectional diameter. The materials and methods used to secure tube $14^{IV}$ to connector 12', and the considerations that impact such a combination, are the same as those disclosed for the combination of tube $14^{IV}$ with connector $12^{IV}$.

Figure 6:
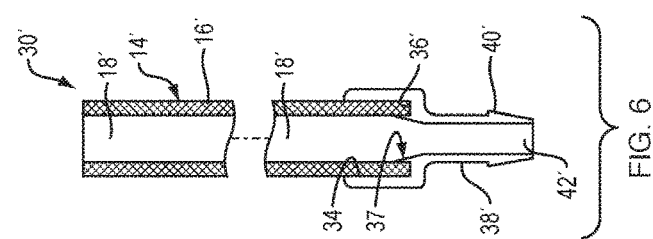
FIG. 6 is a side partial sectional view of a tube/hose barb assembly according to yet another embodiment of the disclosure.

Referring now to FIG. 6, in another aspect of the disclosure, a tube/barb connector assembly shown designated generally as 30' includes a tube designated generally as 14' secured to a barb connector designated generally as 32'. Like connector 12' barb connector 32' has an annular wall 34' that defines a tube bore dimensioned to receive and register against the outer wall of tube 14'. A bottom end of the tube bore is formed as an annular channel, designated generally as 37, and is similar in construction and function to channel 24' of connector 12' in that it has an inner channel wall having a frustoconical shape in cross-section that creates a restriction surface to mechanically lock tube 14' to the connector when bonded to the connector.

A distal end of barb connector 32' is formed as a barb connection 38' with at least one radially extending barb 40'. Barb connection 38' defines a barb lumen 42' that may be dimensioned to be substantially similar in dimension to lumen 18' of tube 14'.

Tube 14' is secured to barb connector 32' in the same manner disclosed for tube/tube connector assembly 10. The materials used to construct barb connector 32' are the same materials disclosed for tube connector 12. The methods used to secure tube 14' to barb connector 32' are the same as those disclosed for tube/tube connector assembly 10. The barb permits connection to other tubes used to deliver or receive liquids, and/or gases depending upon the functional assignment given to the tube/barb connector assembly, i.e., inlet, outlet, vent.

Like tube/tube connector assembly 10, barb connector 32' may secured to a dual-walled, reinforced tube such as dual-walled tube $4^{IV}$ shown in FIGS. 13 and 14. The primary difference is the dimensional modifications needed to receive a tube with a different cross-sectional diameter. The materials and methods used to secure tube $14^{IV}$ to connector 32', and the considerations that impact such a combination, are the same as those disclosed for the combination of tube $14^{IV}$ with connector $12^{IV}$.

Figure 7:
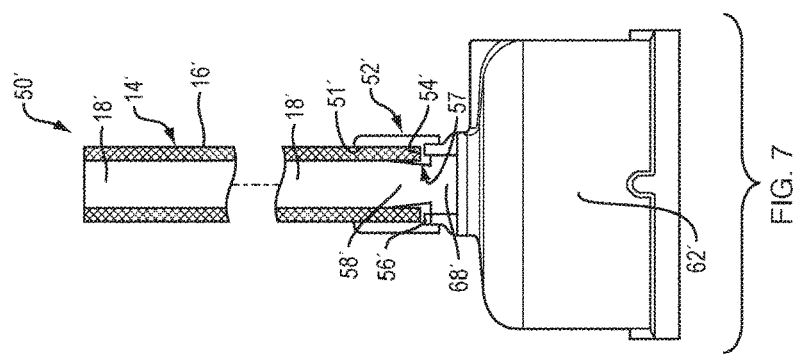
FIG. 7 is a side partial sectional view of a filter capsule/tube/tube connector assembly according to a still further embodiment of the disclosure.

Referring now to FIG. 7, in a further aspect of the disclosure, a tube/tube connector/capsule assembly shown designated generally as 50' includes a tube 14' secured to a tube connector 52' secured to a capsule port 70'. Tube 14' and connector 52' are identical in structure, materials and bonding methods to those disclosed for tube/tube connector assembly 10'. Tube connector 52' has a wall 51' that defines a tube bore 58' dimensioned to receive and register against the outer surface of tube wall 16'. A bottom end of the tube bore is formed as an annular channel, designated generally as 57, and is similar in construction and function to channel 24' of connector 12' in that it has an inner channel wall having a frustoconical shape in cross-section that creates a restriction surface to mechanically lock tube 14' to the connector when bonded to the connector. The bottom surface of channel 24' functions as a stop and registration surface for tube 14' when the tube is inserted in bonded to connector 52'.

A port channel 68' defined by port 70' and a port base 64' is in fluid communication with tube lumen 18' and with the filter chamber defined by capsule 62'. The cross-sectional diameter of channel 68' is dimensioned to be substantially the same as, or not less than the cross-sectional diameter of the tube lumen defined by an unstressed, relaxed segment of tube 14'. A shown in FIG. 7, capsule 62' represents one end of a complete capsule, the remainder of which is not shown for purposes of simplicity. It should be understood that the remainder of the capsule housing will include additional ports that may be configured with tube/tube connector assemblies.

An annular port channel 56 is formed on a distal end of connector 52' and is dimensioned to receive the annular wall of port 70' such that the inner and outer surfaces of the wall register against the walls of annular bore 56'. A top surface of the port wall is further registered against a bottom surface of bore 56' so as to function as a stop and support/registration surface for the joined components.

The materials used to manufacture the tube, tube connector and capsule are the same as those disclosed for tube 14, tube connector 12 and capsule 62 hereinabove. Tube/tube connector/capsule port assembly 50' may be formed in a one-step or two-step process such as those described for assembly 50 herein.

Like tube/tube connector assembly 10, barb connector 52' may be secured to a dual-walled, reinforced tube such as dual-walled tube $14^{IV}$ shown in FIGS. 13 and 14. The primary difference is the dimensional modifications needed to receive a tube with a different cross-sectional diameter. The materials and methods used to secure tube $14^{IV}$ to connector 52', and the considerations that impact such a combination, are the same as those disclosed for the combination of tube $14^{IV}$ with connector $12^{IV}$.

Figure 8:
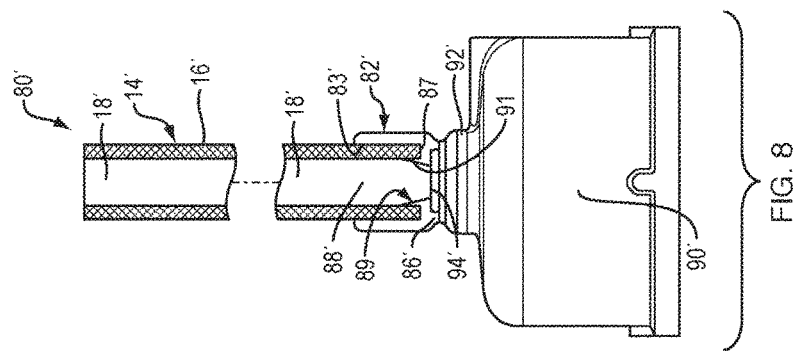
FIG. 8 is a side partial sectional view of a filter capsule/tube/tube connector assembly according to still another embodiment of the disclosure.

Referring now to FIG. 8, in a still further aspect of the disclosure, a tube/tube connector/capsule port assembly is shown designated generally as 80'. Assembly 80' includes tube 14', a tube connector designated generally as 82' and a capsule designated generally as 90'. Connector 82' has the same features and is structured in the same manner as tube connector 12' shown in FIG. 5. Connector 82' has a connector wall 83' that defines a tube bore 88' and is dimensioned to receive and register against the outer surface of tube wall 16'. A bottom end of tube bore 88' is formed as an annular channel, designated generally as 89, and is similar in construction and function to channel 24' of connector 12' in that it has an inner channel wall having a frustoconical shape in cross-section that creates a restriction surface to mechanically lock tube 14' to the connector when bonded to the connector. The bottom surface 87 of channel 89 functions as a stop and registration surface for and end of tube 14' when the tube is inserted into and bonded to connector 82'.

An inner annular surface of the inner wall of annular channel 89 defines a connector channel 91 in fluid communication with a port channel defined by port wall 94' and port base 92' as well of the chamber defined by capsule 90'. The cross-sectional diameter of the narrowest portion of connector channel 91 may be substantially the same as, or not substantially less than the cross-sectional diameter of the lumen of tube 14' taken at a relaxed, unstressed portion of the tube.

A bottom end of connector 82' has an annular wall 86' that defines a bore dimensioned to receive the outer wall of capsule port 94'. This connector/port connection differs from the connector/port connection shown in FIG. 7 in that connector 82' does not define an annular channel to receive the inner and outer surfaces of the port wall, but just a bore to receive and register against the outer surface of the port wall. This provides a less robust connection, but an adequate one to handle the applications to which the capsule is put to use as well as the post-use sterilization procedures. Like tube/tube connector/capsule port assembly 50', tube/tube connector/capsule port assembly 80' can be constructed from the same materials disclosed for the components of assembly 50 in either a one-step or two-step process such as those disclosed for assembly 50.

Like tube/tube connector assembly 10, barb connector 82' may be secured to a dual-walled, reinforced tube such as dual-walled tube 14$^{IV}$ shown in FIGS. 13 and 14. The primary difference is the dimensional modifications needed to receive a tube with a different cross-sectional diameter. The materials and methods used to secure tube 14$^{IV}$ to connector 82', and the considerations that impact such a combination, are the same as those disclosed for the combination of tube 14$^{IV}$ with connector 12$^{IV}$.

Figure 9:
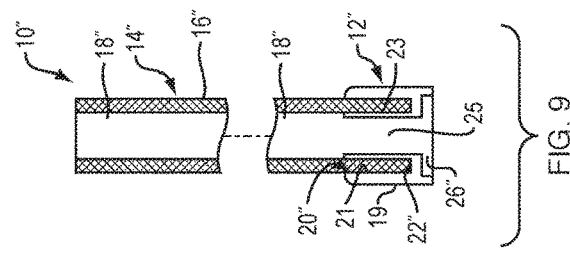
FIG. 9 is a side partial sectional view of a tube/tube connector assembly according to yet another embodiment of the disclosure.

Referring to FIG. 9, in one aspect of the disclosure, a tube/connector assembly shown designated generally as 10" includes a tube designated generally as 14" secured to a tube connector designated generally as 12". Tube 14" has an annular wall 16" that defines a lumen 18" like tube 14 disclosed herein.

Connector 12" has an annular wall 19 that defines a tube channel designated generally as 20" dimensioned to receive and register against the inner and outer walls of tube 14". Tube channel 20" comprises a channel outer wall 21", an annular channel bottom 22" and a channel inner wall 23". Annular channel bottom 22" forms a mechanical stop for the tube rid when inserted into connector 12". This configuration creates a tube rigidifying structure that mechanically enhances the segment of the tube secured in the channel. When thermal bonding is applied and the tube material is allowed to flow and expand in the channel, the tube is radially restricted by the walls of the channel to maintain the cross-sectional dimensional integrity of tube 14". The cross-sectional diameter of a tube bore 25 defined by an inner surface of inner wall channel 23" may be dimensioned to be substantially similar to, or essentially not less than the cross-sectional diameter of the lumen of a relaxed or unstressed segment of tube 14".

A second capsule bore 26" is formed on a bottom end of connector 12" and dimensioned to receive a capsule port (disclosed in more detail below. Capsule bore 26" is in fluid communication with tube bore 25 (defined by an inner surface of channel inner wall 23") and tube lumen 18" when the tube is secured to the connector. Tube/tube connector assembly 10" is structured to be bonded directly to a capsule port and is formed in a two-step process like assembly 10 whereby the tube and connector are bonded in one process step and the tube/tube connector assembly is bonded to the capsule in a second process step. In an, alternative embodiment, the tube, tube connector and capsule port are bonded together in a single processing step when the capsule is molded as disclosed more fully herein.

Tube 14" may be constructed from same materials disclosed for tube 14. Tube connector 12" may be constructed from the same materials disclosed for tube connector 12.

Like tube/tube connector assembly 10, barb connector 12" may be secured to a dual-walled, reinforced tube such as dual-walled tube 14$^{IV}$ shown in FIGS. 13 and 14. The primary difference is the dimensional modifications needed to receive a tube with a different cross-sectional diameter. The materials and methods used to secure tube 14$^{IV}$ to connector 12', and the considerations that impact such a combination, are the same as those disclosed for the combination of tube 14$^{IV}$ with connector 12$^{IV}$.

Figure 10:
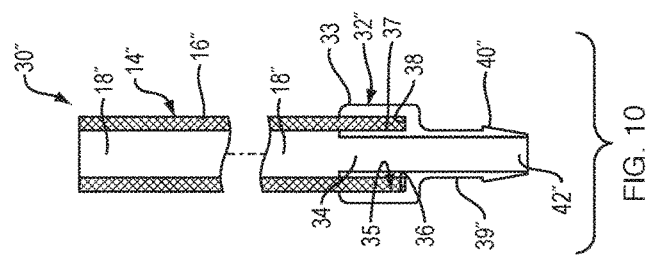
FIG. 10 is a side partial sectional view of a tube/tube barb assembly according to a further embodiment of the disclosure.

Referring now to FIG. 10, in another aspect of the disclosure, a tube/barb connector assembly shown designated generally as 30" includes a tube designated generally as 14" secured to a barb connector designated generally as 32". Like connector 12", barb connector 32" has an annular wall 33 that defines a tube channel designated generally as 35 dimensioned to receive and register against the inner and outer walls of tube 14". Tube channel 35 comprises a channel outer wall 36, an annular channel bottom 38 and a channel inner wall 37. Annular channel bottom 38 forms a mechanical stop for the tube end when inserted into connector 32". Again, this configuration creates a tube rigidifying structure that mechanically enhances the segment of the tube secured in the channel.

When thermal bonding is applied and the tube material is allowed to flow and expand in the channel, the tube is radially restricted by the walls of the channel to maintain the cross-sectional dimensional integrity of tube 14", The cross-sectional diameter of a tube bore 34 defined by an inner surface of inner wall channel 37 may be dimensioned to be substantially similar to, or essentially not less than the cross-sectional diameter of the tube lumen at a relaxed or unstressed segment of tube 14".

A distal end of barb connector 32" is formed as a barb connection 39 with at least one radially extending barb 40". Barb connection 39 defines a barb lumen 42" that may have a cross-sectional diameter substantially similar to the cross-sectional diameter of lumen 18" at a relaxed or unstressed portion of tube 14".

Tube 14" is secured to barb connector 32" in the same manner disclosed for tube/tube connector assembly 10. The materials used to construct barb connector 32" are the same materials disclosed for tube connector 12. The methods used to secure tube 14" to barb connector 32" are the same as those disclosed for tube/tube connector assembly 10. The barb permits connection to other tubes used to deliver or receive liquids and/or gases depending upon the functional assignment given to the tube/barb connector assembly, i.e., inlet, outlet, vent.

Like tube/tube connector assembly 10, barb connector 32" may be secured to a dual-walled, reinforced tube such as dual-walled tube 14$^{IV}$ shown in FIGS. 13 and 14. The primary difference is the dimensional modifications needed to receive a tube with a different cross-sectional diameter. The materials and methods used to secure tube 14$^{IV}$ to connector 32", and the considerations that impact such a combination, are the same as those disclosed for the combination of tube 14$^{IV}$ with connector 12$^{IV}$.

Figure 11:
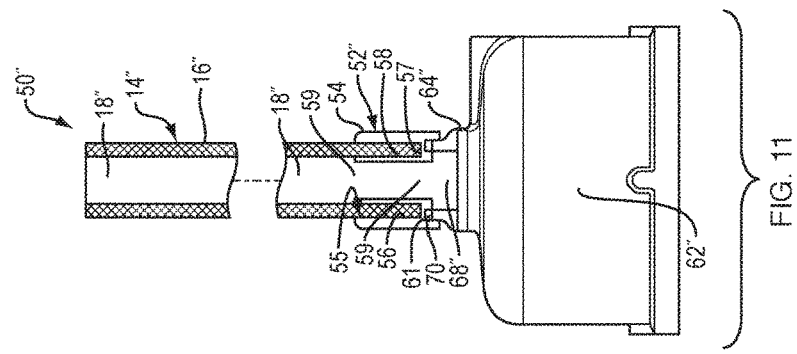
FIG. 11 is a side partial sectional view of a tube/tube connector/filter capsule assembly according to a still further embodiment of the disclosure.

Referring now to FIG. 11, in a further aspect of the disclosure, a tube/tube connector/capsule assembly shown designated generally as 50" includes a tube 14" secured to a tube connector 52" secured to a capsule port 70". Tube 14" and connector 52" are identical in structure, materials and bonding methods to those disclosed for tube/tube connector assembly 10". Tube connector 52" has an annular wall 54 that defines an annular tube channel designated generally as 55 dimensioned to receive and register against the inner and outer walls of tube 14". Tube channel 55 comprises a channel outer wall 56, an annular channel bottom 57 and a channel inner wall 58. Annular channel bottom 57 forms a mechanical stop and registration surface for the tube end when inserted into, and bonded to, connector 52".

Like the similar structures disclosed herein for assembly 10", this configuration creates a tube rigidifying structure that mechanically enhances the segment of the tube secured in the channel. When thermal bonding is applied and the tube material is allowed to flow and expand in the channel, the tube is radially restricted by the wall of the channel to maintain the cross-sectional dimensional integrity of tube 14". The cross-sectional diameter of a tube bore 59 defined by an inner surface of inner wall channel 58 may be dimensioned to be substantially similar to, or essentially not less than the cross-sectional diameter of the tube lumen at a relaxed or unstressed segment of tube 14".

A port channel 68" defined by port 70" and a port base 64" is in fluid communication with tube lumen 18' and with the filter chamber defined by capsule 62". The cross-sectional diameter of channel 68" may be dimensioned to be substantial y the same as, or not less than the cross-sectional diameter of tube lumen 18" defined at an unstressed, relaxed segment of tube 14'. As shown in FIG. 11, capsule 62" represents one end of a complete capsule, the remainder of which is not shown for purposes of simplicity. It should be understood that the remainder of the capsule housing will include additional ports that may be configured with tube/tube connector assemblies.

An annular port bore 61 is formed on a distal end of connector 52" and is dimensioned to receive the annular wall of port 70" such that the inner and outer surfaces of the wall register against the walls of port bore 61. A top surface of the port wall is further registered against a bottom surface of bore 61 so as to function as a stop and support/registration surface for the joined components.

The materials used to manufacture the tube/tube connector/capsule assembly 50" are the same as those disclosed for tube 14, tube connector 12 and capsule 62 hereinabove. Assembly 50' may be formed in a one-step or two-step process such as those described for assembly 50 herein.

Like tube/tube, connector assembly 10, barb connector 52" may be secured to a dual-walled, reinforced tube such as dual-walled tube 14$^{IV}$ shown in FIGS. 13 and 14. The primary difference is the dimensional modifications needed to receive a tube with a different cross-sectional diameter. The materials and methods used to secure tube 14$^{IV}$ to connector 52", and the considerations that impact such a combination are the same as those disclosed for the combination of tube 14$^{IV}$ with connector 12$^{IV}$.

Figure 12:
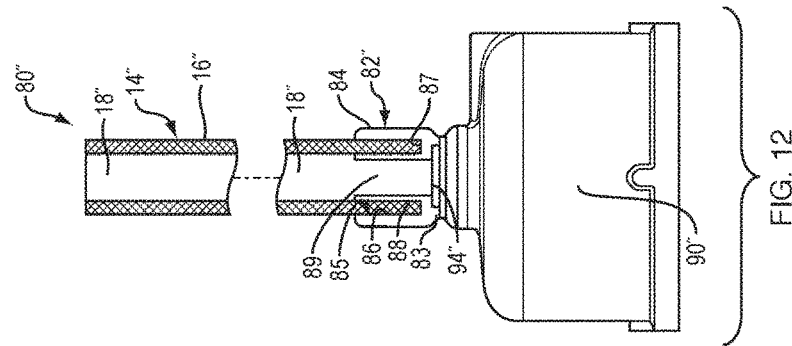
FIG. 12 is a side partial sectional view of a tube/tube connector filter capsule assembly according to yet another embodiment of the disclosure.

Referring now to FIG. 12, in a still further aspect of the disclosure, a tube/tube connector/capsule port assembly is shown designated generally as 80". Assembly 80" includes tube 14", a tube connector designated generally as 82" and a capsule designated generally as 90". Connector 82" has the same features and is structured in the same manner as tube connector 12" shown in FIG. 9.

Connector 82' has a connector wall 83 that an annular tube channel designated generally as 85 dimensioned to receive and register against the inner and outer walls of tube 14". Tube channel 85 comprises a channel outer wall 86, an annular channel bottom 87 and a channel inner wall 88. Annular channel bottom 87 forms a mechanical stop and registration surface for the tube end when inserted into, and bonded to, connector 82". Like the similar structures disclosed herein for assembly 10", this configuration creates a tube rigidifying structure that mechanically enhances the segment of the tube secured in the channel. When thermal bonding is applied and the tube material is allowed to flow and expand in the channel, the tube is radially restricted by the walls of the channel to maintain the cross-sectional dimensional integrity of tube 14". The cross-sectional diameter of a tube bore 89 defined by an inner surface of inner wall channel 88 may be dimensioned to be substantially similar to, or essentially not less than the cross-sectional diameter of the tube lumen at a relaxed or unstressed segment of tube 14".

A bottom end of connector 82" has an annular wall 83 that defines a bore dimensioned to receive the outer wall of capsule port 94". This connector/port connection differs from the connector/port connection shown in FIG. 11 in that connector 82" does not define an annular channel to receive the inner and outer surfaces of the port wall, but just a bore to receive and register against the outer surface of the port wall. This provides a less robust connection, but an adequate one to handle the applications to which the capsule is put to use as well as the post-use sterilization procedures. Like tube/tube connector/capsule port assembly 50", tube/tube connector/capsule port assembly 80" can be constructed from the same materials disclosed for the components of assembly 50 in either a one-step or two-step process such as those disclosed for assembly 50.

Like tube/tube connector assembly 10, barb connector 82" may be secured to a dual-walled, reinforced tube such as dual-walled tube 14$^{IV}$ shown in FIGS. 13 and 14. The primary difference is the dimensional modifications needed to receive a tube with a different cross-sectional diameter. The materials and methods used to secure tube 14$^{IV}$ to connector 82", and the considerations that impact such a combination, are the same as those disclosed for the combination of tube 14$^{IV}$ with connector 12$^{IV}$.

Figure 19:
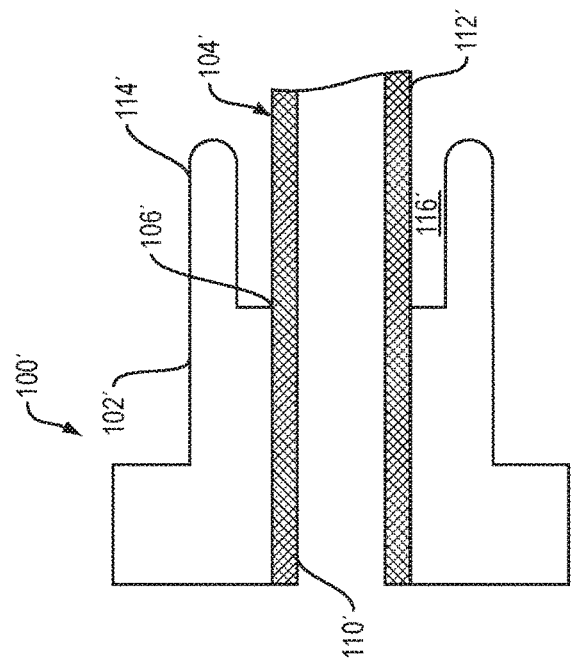
FIG. 19 is a side sectional view of a single-walled tube/tube connector subassembly with a reinforcement collar according to another embodiment the disclosure.
Figure 18:
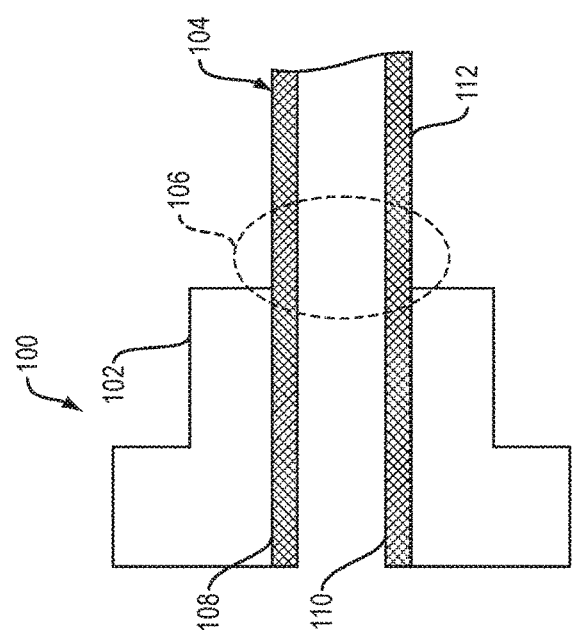
FIG. 18 is a side sectional view of a single-walled tube/tube connector subassembly according to one embodiment of the disclosure.

Referring now to FIGS. 18 and 19, in another aspect of the disclosure, a connector modification is formed to provide stress relief to the connector/tube junction. As shown in the figures, a connector/tube assembly shown designated generally as 100 includes a connector 102 secured about a tube 104. As highlighted in FIG. 18, the connector/tube junction 106 creates a weak zone where the support of connector 102 ends. This is a flexion point with the connector functioning as an anchor 108 to the supported segment of the tube 110 against which the unsupported segment of the tube 112 particularly as the junction, can bend and become weakened.

To limit the degree of flexion, as shown in FIG. 18, a modified connector/tube assembly designated generally as 100' has the same basic features as assembly 100. A connector 102' is secured to a segment 110' of a tube 104'. A flexion zone is formed at the connector/tube junction 106'. This leaves an unsupported tube segment 112'. To support the flexion zone, an annular tube support collar 114' is formed extending from the peripheral end of connector 102'. The gap 116' between collar 114' and tube 104' permits some flexion and range of motion for the tube to accommodate any need to direct the tube away from a perpendicular orientation to the connector when connected to a larger assembly (not shown). The length of support collar 114' can be adjusted to increase or decrease the range of tube flexion permitted. A shorter collar will permit a greater range of flexion while a longer collar will permit a relatively shorter range of tube flexion. Optionally, an additional ring (not shown) may be formed about the collar from reinforcing material, e.g., metal, to provide additional rigidity, if needed.

While the present disclosure has been described in connection with several embodiments thereof, it will be apparent to those skilled in the art that many changes and modifications may be made without departing from the true spirit and scope of the present disclosure. Accordingly, it is intended by the appended claims to cover all such changes and modifications as come within the true spirit and scope of the disclosure.

What we claim as new and desire to secure by United States Letters Patent is:

1. A filter capsule-tube assembly comprising:
   a shell having a housing wall defining a filter chamber with at least one port formed on the housing wall, extending axially from the housing wall, and defining a port channel in fluid communication with the filter chamber, wherein the at least one port has an outer wall surface and an outer cross-sectional diameter less than the outer cross-sectional diameter of the housing wall;

a rigid tube connector defining a connector bore and having portions defining a tube-receiving bore and portions defining a capsule port-receiving bore with an inner bore wall defining the port-receiving bore, wherein the tube connector is secured to the outer wall surface of the at least one port via registration with the inner bore wall of the port-receiving bore; and, a flexible tube defining a lumen bonded to the tube connector with an end of the tube secured in the tube-receiving bore and separated structurally from the at least one port, wherein the connector bore, tube lumen and port bore are in fluid communication.

2. The filter capsule-tube assembly of claim 1, wherein the connector bore has a cross-sectional diameter substantially the same as the cross-sectional diameter of the tube lumen at a relaxed, or unstressed portion of the tube.

3. The filter capsule-tube assembly of claim 1, wherein the tube comprises an inner tube and an outer tube superposed about the inner tube to form a dual-walled tube.

4. The filter capsule-tube assembly of claim 3, wherein at least one of the inner and outer tubes is formed with reinforcement material.

5. The filter capsule-tube assembly of claim 4, wherein a segment of the outer tube is removed to expose an outer surface of the inner tube, wherein the exposed outer surface of the inner tube is registered against the tube receiving bore.

6. The filter capsule-tube assembly of claim 1 further comprising an annular tube support collar extending from a peripheral edge of the tube connector and surrounding a tube connector/tube joint.

7. The filter capsule of claim 1 wherein the tube is made from a material selected from the group consisting of TPE, TPR, PVS, PVC, silicone, and combinations thereof.

8. The filter capsule of claim 2 wherein the tube connector is made from a material selected from the group consisting of PP, PE, HDPE, Nylon, PVC, Hytrel and combinations thereof.

9. A filter capsule-tube assembly comprising:

a shell having a housing wall defining a filter chamber with at least one port stem formed on the housing wall, extending axially from the housing wall, and defining a port channel in fluid communication with the filter chamber, wherein the at least one port has an outer wall surface and an outer cross-sectional diameter less than the outer cross-sectional diameter of the housing wall;

a rigid tube connector having portions defining an annular tube-receiving channel and portions defining a capsule-port-receiving bore with an inner bore wall defining the port-receiving bore, wherein an inner channel wall that partially defines the tube receiving channel defines a connector bore, wherein the tube connector is secured to the outer wall surface of the at least one port via registration with the inner bore wall of the port-receiving bore; and, a flexible tube defining a lumen thermally bonded to the tube connector with an end of the tube secured in the tube receiving channel and separated structurally from the at least one port, wherein the connector bore, tube lumen and port bore are in fluid communication.

10. The filter capsule-tube assembly of claim 9, wherein the connector bore has a cross-sectional diameter substantially the same as the cross-sectional diameter of the tube lumen at a relaxed, or unstressed portion of the tube.

11. The filter capsule-tube assembly of claim 9, wherein the tube comprises an inner tube and an outer tube superposed about the inner tube to form a dual-walled tube.

12. The filter capsule-tube assembly of claim 11, wherein at least one of the inner and outer tubes is formed with reinforcement material.

13. The filter capsule-tube assembly of claim 12, wherein a segment of the outer tube is removed to expose an outer surface of the inner tube, wherein the exposed outer surface of the inner tube is registered against the tube receiving bore.

14. The filter capsule-tube assembly of claim 9 further comprising an annular tube support collar extending from a peripheral edge of the tube connector and surrounding a tube connector/tube joint.

15. A filter capsule-tube assembly comprising:

a shell having a housing wall defining a filter chamber with at least one port stem defining a port channel formed on the shell that defines a channel in fluid communication with the filter chamber;

a rigid tube connector having portions defining an annular tube receiving channel and portions defining a capsule port stem receiving bore, wherein the tube receiving channel is partially defined by an inner channel wall that has an inner surface defining a frustoconical segment in cross-section defining a connector bore with the smaller diameter end of the segment positioned proximally to the shell, wherein the tube connector is secured to the at least one port stem via the port receiving bore; and, a flexible tube defining a lumen bonded to the tube connector with an end of the tube secured in the tube receiving channel, wherein the connector bore, tube lumen and port bore are in fluid communication.

16. The filter capsule-tube assembly of claim 15, wherein the smaller diameter end of the connector bore has a cross-sectional diameter substantially the same as the cross-sectional diameter of the tube lumen at a relaxed, or unstressed portion of the tube.

17. The filter capsule-tube assembly of claim 15, wherein the tube comprises an inner tube and an outer tube superposed about the inner tube to form a dual-walled tube.

18. The filter capsule-tube assembly of claim 17, wherein at least one of the inner and outer tubes is formed with reinforcement material.

19. The filter capsule-tube assembly of claim 18, wherein a segment of the outer tube is removed to expose an outer surface of the inner tube, wherein the exposed outer surface of the inner tube is registered against the tube receiving bore.

20. The filter capsule-tube assembly of claim 15 further comprising an annular tube support collar extending from a peripheral edge of the tube connector and surrounding a tube connector/tube joint.

* * * * *